US006610305B1

(12) United States Patent
Elbers et al.

(10) Patent No.: US 6,610,305 B1
(45) Date of Patent: Aug. 26, 2003

(54) SAFE ATTENUATED BOVINE VIRAL DIARRHEA VIRUSES FOR USE IN PREGNANT COWS

(75) Inventors: Knut Elbers, Gau-Algesheim (DE); Gregor Meyers, Walddorfhaeslach (DE)

(73) Assignee: Boehringer Ingelheim Vetmedica GmbH, Ingelheim (DE)

( * ) Notice: Subject to any disclaimer, the term of this patent is extended or adjusted under 35 U.S.C. 154(b) by 67 days.

(21) Appl. No.: 09/706,649

(22) Filed: Nov. 6, 2000

Related U.S. Application Data

(60) Provisional application No. 60/170,616, filed on Dec. 14, 1999.

(30) Foreign Application Priority Data

Nov. 30, 1999 (DE) ............................................. 99123767

(51) Int. Cl.$^7$ ................................................. C12N 7/00
(52) U.S. Cl. ................................. 424/218.1; 424/204.1; 435/235.1; 530/395; 530/826
(58) Field of Search ................................. 530/395, 826; 435/235.1; 424/204.1, 218.1

(56) References Cited

FOREIGN PATENT DOCUMENTS

| EP | 0965639 A1 | 12/1999 |
| WO | WO-9512682 A2 | 5/1995 |

OTHER PUBLICATIONS

Fields. *Fields Virology*, 3$^{rd}$ edition, (Philadelphia, PA, Lippincott Williams & Wilkins, 1995), pp. 1059. QR360. V5125.*

Cruse et al. *Illustrated Dictionary of Immunology* (Boca Raton, FL, CRC Press, Inc., 1995), p. 309. QR180.4.C78.*

Paul *Fundamental Immunology*, (Philadelphia & New York, Lippincott–Raven Publishers, 1993), pp. 1311–1312 QR181.F84.*

Vassilev, Ventzislav B. et al; "Authenic and Chimeric Full-–Length Genomic cDNA Clones of Bovine Viral Diarrhea Virus that Yield Inectious Transcripts"; Journal of Virology; Jan. 1997; vol. 71; No. 1; 471–478; XP 002144456.

Hulst, M.M. et al; "Inactivation of the RNase Activity of Glycoprotein Erns of Classical Swine Fever Virus Results in a Cytopathogenic Virus"; Journal of Virology; Jan. 1998; 151–157; vol. 72; No. 1; XP002086212.

Windisch, Joerg M. et al; "RNase of Classical Swine Fever Virus: Biochemical Characterization and Inhibition by Virus–Neutralizing Monoclonal Antibodies"; Journal of Virology; Jan. 1996; 352–358; vol. 70, No. 1; XP–002095267.

* cited by examiner

*Primary Examiner*—Jeffrey Stucker
(74) *Attorney, Agent, or Firm*—Robert P. Raymond; Timothy X. Witkowski; Mary-Ellen Devlin

(57) ABSTRACT

This invention relates to the use of specifically attenuated live BVD (bovine viral diarrhea) viruses for the preparation of a vaccine for use in the prevention and/or treatment of BVDV infections in breeding stocks of cattle, pregnant cows and for fetal protection in pregnant cows.

16 Claims, No Drawings

SAFE ATTENUATED BOVINE VIRAL DIARRHEA VIRUSES FOR USE IN PREGNANT COWS

RELATED APPLICATIONS

Benefit of U.S. Provisional Application Serial No. 60/170,616, filed on Dec. 14, 1999 is hereby claimed.

FIELD OF THE INVENTION

The present invention relates to the use of specifically attenuated live BVD (Bovine Viral Diarrhea) viruses for the preparation of a vaccine for use in the prevention and/or treatment of BVDV infections in breeding stocks of cattle, pregnant cows and for fetal protection in pregnant cows.

The invention also relates to a method of treatment and/or prevention of BVDV infections in the above named group of cattle.

BACKGROUND OF THE INVENTION

Bovine Viral Diarrhea Virus (BVDV) is the causative agent of BVD and mucosal disease in cattle (Baker, 1987; Moennig and Plagemann, 1992; Thiel et al., 1996). Fetal infection during pregnancy can result in the resorption of the fetus, abortions as well as birth of immunotolerant calves which are persistently infected with BVDV. These calves lack or have very low neutralizing antibody titers and are continuously shedding high amounts of virus. Next to acute or persistently infected bulls these calves are the major source for virus spreading and are therefore of primary importance in the epidemiology of this disease. The major economical impact of BVD results from high abortion rates, stillbirths, fetal resorption, mummification, congenital malformations, and birth of weak and undersized calves. For a detailed review of the pathogenesis, the article of Moennig and Liess of 1995 should be referred to in its entirety.

Two major antigenic groups of BVDV (type I and II) have been described (Becher et al. 1999) which display limited cross neutralizing antibody reactions (Ridpath et al. 1994).

BVDV and other pestiviruses share the ability to cross the placenta of pregnant host animals. Present attenuated live BVDV vaccines also cross the placenta of seronegative heifers and result in clinical symptoms of wild type BVDV infections (see Moennig and Liess, Orban et al. 1983; Liess et al. 1984).

Present vaccines for the prevention and treatment of BVDV infections still have drawbacks (Oirschot et al. 1999).

Killed vaccines (inactivated whole virus) or subunit vaccines (conventionally purified or heterologously expressed purified viral proteins) are most often inferior to live vaccines in their efficacy to produce a full protective immune response even in the presence of adjuvants.

Live BVDV vaccines, although attenuated, are most often associated with serious safety problems. As mentioned above, they cross the placenta of pregnant cows and lead to clinical manifestations in the fetus and/or the induction of persistently infected calves. Therefore, they cannot be applied to breeding herds that comprise pregnant cows. Pregnant cows must to be kept isolated from vaccinated cattle to protect fetuses and may not be vaccinated themselves. Furthermore, revertants of attenuated live BVDV pose a serious threat to cattle. For conventionally derived attenuated viruses wherein the attenuation is attained by conventional multiple passaging, the molecular origin as well as the genetic stability remains unknown and the outbreak of revertants is unpredictable.

Live vaccines with defined mutations as a basis for attenuation would allow to avoid the disadvantages of the present generation of attenuated vaccines. A further advantage of said attenuating mutations lies in their molecular uniqueness which allows for use as distinctive labels for an attenuated pestiviruses and to distinguish them from pestiviruses from the field.

Such live and specifically attenuated pestiviruses with a high potential for induction of immunity as well as a defined basis of attenuation which can also be distinguished from pathogenic pestiviruses are described in the PCT-application PCT/EP 99/03642. In this application it has been demonstrated that pestiviruses can be specifically attenuated by the inactivation of the RNase activity residing in glycoprotein $E^{RNS}$. The inventors disclose that this attenuation principle is universal to all pestiviruses and particularly suitable for BVDV.

This application discloses an attenuated live vaccine that is superior in its efficacy of induction of immunity to subunit and killed vaccines as well as superior to conventionally attenuated vaccines which are molecularly undefined, unmarked and unpredictable With respect to mutants. From prior art an expert would naturally associate the risk of fetal BVDV infection when vaccinating pregnant cows or cattle in the near vicinity of pregnant cows with an attenuated live virus. This remains a serious drawback limiting the use of such a vaccine.

Therefore, the technical problem underlying this invention was to provide safely attenuated and live BVDV vaccines that can be used for the preparation of a live vaccine for use in the prevention and/or treatment of BVDV infections of pregnant cows or cattle in the presence of pregnant cows.

BRIEF DESCRIPTION OF THE FIGURE

FIG. 1 shows the amino acid sequence of the glycoprotein $E^{RNS}$ of BVDV CP VII (CP7) corresponding to residues 271 to 497 of the CP7 polyprotein.

DISCLOSURE OF THE INVENTION

The solution to the above technical problem is achieved by the description and the embodiments characterized in the claims.

It has surprisingly been found that live BVDV (bovine viral diarrhea virus), wherein the RNase activity residing in its glycoprotein $E^{RNS}$ is inactivated, does not result in placental transmission to the fetus when pregnant cows are vaccinated with said viruses. No clinical signs in the calves are observable when a BVDV strain of said characteristic is used to challenge pregnant cows.

Therefore, in one aspect, the present invention relates the unexpected use of a live BVDV (bovine viral diarrhea virus), wherein the RNase activity residing in its glycoprotein $E^{RNS}$ is inactivated, for the preparation of a live vaccine for use in the prevention and/or treatment of BVDV infections in breeding stocks of cattle.

Even more unexpected, pregnant cows themselves may be vaccinated with said specifically attenuated BVDV. Consequently, in a preferred embodiment, the present invention relates to the use of said BVDV for the preparation of a live vaccine for use in the prevention and/or treatment of BVDV infections in pregnant cows.

This allows for the first time ever to prevent and protect the fetus itself against BVDV infections with a live vaccine. In a more preferred embodiment, the present invention relates to the use of said BVDV for the preparation of a live vaccine for inducing fetal protection against BVDV infections in pregnant cows.

The term "vaccine" as used herein refers to a pharmaceutical composition comprising at least one immunologically active component that induces an immunological response in an animal and possibly, but not necessarily, one or more additional components that enhance the immunological activity of said active component. A vaccine may additionally comprise further components typical to pharmaceutical compositions. The immunologically active component of a vaccine may comprise complete live organisms in either its original form or as attenuated organisms in a so-called modified live vaccine (MLV) or organisms inactivated by appropriate methods in a so-called killed vaccine (KV). In another form, the immunologically active component of a vaccine may comprise appropriate elements of said organisms (subunit vaccines) whereby these elements are generated either by destroying the whole organism or the growth cultures of such organisms and subsequent purification steps yielding in the desired structure(s), or by synthetic processes induced by an appropriate manipulation of a suitable system such as, but not restricted to, bacteria, insects, mammalian, or other species, plus subsequent isolation and purification procedures or by induction of said synthetic processes in the animal needing a vaccine by direct incorporation of genetic material using suitable pharmaceutical compositions (polynucleotide vaccination). A vaccine may comprise one or simultaneously more than one of the elements described above.

Additional components to enhance the immune response are constituents commonly referred to as adjuvants, like e.g. aluminiumhydroxide, mineral or other oils or ancillary molecules added to the vaccine or generated by the body after the respective induction by such additional components, like but not restricted to interferons, interleukins or growth factors.

A "pharmaceutical composition" essentially consists of one or more ingredients capable of modifying physiological e.g. immunological functions of the organism it is administered to, or of organisms living in or on its surface like but not restricted to antibiotics or antiparasitics, as well as other constituents added to it in order to achieve certain other objectives like, but not limited to, processing traits, sterility, stability, feasibility to administer the composition via enteral or parenteral routes such as oral, intranasal, intravenous, intramuscular, subcutaneous, intradermal or other suitable route, tolerance after administration, controlled release properties.

A vaccine of the invention refers to a vaccine as defined above, wherein one immunologically active component is a live BVDV, wherein the RNase activity in its protein $E^{RNS}$ is inactivated.

The term "live vaccine" refers to a vaccine comprising a living, in particular, a living viral active component.

The term "BVDV" as used herein refers to all viruses belonging to species BVDV 1 and BVDV 2 in the genus pestivirus within the family Flaviviridae (Becher et al. 1999).

The more classical BVDV type I strains and the more recently recognized BVDV type II strains display some limited but distinctive differences in nucleotide and amino acid sequences. These differences are immunologically distinguishable by monoclonal antibodies. The attenuation principle of inactivating the RNase activity in the protein $E^{RNS}$ as described in the above referenced international application is universally applicable and holds true for both type I and type II BVDV. The surprising feature of BVDV which are attenuated in said manner that these viruses do not cross the placental barrier and do not lead to clinical manifestations of BVDV infections in the fetus applies to all types of BVDV. Therefore, in a further more preferred embodiment the present invention relates to the use of said BVDV for the preparation of a live vaccine for the treatment and or prevention of fetal infection, pregnant cows and breeding stocks of cattle.

"RNase activity" as used herein refers to the ability of the glycoprotein $E^{RNS}$ which is an inherent protein to all naturally occurring pestiviruses such as BVDV to hydrolyze RNA.

It should be noted that the term glycoprotein E0 is often used synonymously to glycoprotein $E^{RNS}$ in publications.

The term "inactivation of the RNase activity residing in said glycoprotein" refers to the inability or reduced capability of a modified glycoprotein $E^{RNS}$ to hydrolyze RNA as compared to the unmodified wild type of said glycoprotein $E^{RNS}$.

Inactivation of the RNase activity residing in glycoprotein $E^{RNS}$ can be achieved by deletions and/or mutations of at least one amino acid of said glycoprotein as demonstrated in the international application PCT/EP99/03642 and by Hulst et al. (1998). Therefore, in a most preferred embodiment the present invention relates to the use of live BVDV, wherein said RNase activity is inactivated by deletions and/or mutations of at least one amino acid of said glycoprotein.

The amino acid sequence for the BVDV strain CP7 is accessible for reference purposes in the GenBank/EMBL data library (accession number U63479). Two regions of amino acids are highly conserved in glycoprotein $E^{RNS}$ as well as in some plant and fungal RNase-active proteins (Schneider et al., 1993). These two regions are of particular importance to the RNase enzymatic activity. The first region consists of the region at the amino acids at position 298 to 310 and the second region consists of the amino acids at position 341 to 360 of said viral polyprotein as exemplified for the CP7 strain of BVDV (numbering according to the deduced amino acid sequence of the CP7 strain; see FIG. 1 (SEQ ID NO: 9) for the amino acid sequence of the CP7 glycoprotein $E^{RNS}$). The amino acids of particular importance to the RNase activity as mentioned above are by no means limited to the exact position as defined for the CP7 strain of BVDV but are simply used in an exemplary manner to point out the preferred amino acids being at that position or corresponding to that position in BVDV strains since they are highly conserved. For different BVDV pestiviruses, the numbering of the positions of the preferred amino acids might be different but an expert in the field of the molecular biology of pestiviruses will easily identify these preferred amino acids by their position relative to the highly conserved amino acids of said glycoprotein.

As a consequence, the present invention relates in a more preferred embodiment to the use of BVDV according to the invention, wherein said inactivating deletions and/or mutations are located at the amino acids at position 298 to 310 and/or position 341 to 360, as described for the BVDV CP7 strain in an exemplary manner and corresponding thereto in other BVDV strains, of said glycoprotein.

In a most preferred embodiment the present invention discloses the use of a live BVD virus according to the invention wherein said RNase activity is inactivated by the deletion of the histidine residue at the position 349 as described for the CP7 strain of BVDV in an exemplary manner or corresponding thereto in other BVDV strains, of said glycoprotein.

In a further aspect the invention relates to a method for the prevention and/or treatment of BVDV infections in breeding stocks of cattle characterized in that a pharmaceutical composition comprising a live BVD virus, wherein the RNase activity residing in its glycoprotein $E^{RNS}$ is inactivated, is applied to an animal in need of such prophylaxis or treatment.

To practice the invention it is necessary to prepare a BVDV according to the invention. This can be done with any available BVDV that is suited for recombinant modification. One example how to obtain such a virus according to the invention is given below in example 2. The example demonstrates the preparation of a virus for a use according to the invention in an exemplary manner and is by no means limiting. An expert in the field of virology or molecular biology can achieve this by standard methods which are abundantly provided in the art.

The application of the preferred live viruses according to the application to the preferred group of animals is identical to the application methods which are available and practiced for other live attenuated viruses in the art.

References

1. Baker, J. C. 1987. Bovine viral diarrhea virus: a review. J. Am. Vet. Med.Assoc. 190: 1449–1458.
2. Becher, P., Orlich, M., Kosmidou A., König, M., Baroth M., Thiel H. J., 1999. Genetic Diversity of Pestivirus: Identification of Novel Groups and Implications for Classification. Virology 262: 64–71.
3. Fuerst T. R. et al. 1986. Eukaryotic transient expression system based on recombinant vaccinia virus that synthesizes bacteriophage T7 RNA polymerase. Proc. Natl. Acad. Sci. 83: 8122–8126.
4. Hulst, M. M., F. E. Panoto, A. Hooekmann, H. G. P. van Gennip., and Moormann, R. J. M. 1998. Inactivation of the RNase activity of glycoprotein $E^{rns}$ of classical swine fever virus results in a cytopathogenic virus. J. Virol. 72: 151–157.
5. Kunkel, T. A., J. D. Roberts, and R. A. Zakour. 1987. Rapid and efficient site-specific mutagenesis without phenotypic selection. Methods Enzymol. 154:367–392.
6. Meyers, G., Tautz, N., Becher, P., Thiel, H.-J., & Kümmerer, B. M. 1996b. Recovery of cytopathogenic and noncytopathogenic bovine viral diarrhea viruses from cDNA constructs. J. Virol., 70: 8606–8613.
7. Meyers, G., Thiel, H.-J., and Rümenapf, T. 1996a. Classical swine fever virus: Recovery of infectious viruses from cDNA constructs and generation of recombinant cytopathogenic swine fever virus. J. Virol. 67:7088–709526.
8. Moennig, V. and Plagemann, J. 1992. The pestiviruses. Adv. Virus Res. 41: 53–91.
9. Moennig, V. and Liess, B. 1995. Pathogenesis of Intrauterine Infections with Bovine Viral Diarrhea Virus. 11: (3), 477–487.
10. Oirschot van, J. T., Bruschke, C. J. M., Rijn van, P. A., 1999. Vaccination of cattle against bovine viral diarrhoea. Veterinary Microbiology, 64: 169–183.
11. Sandvik, T., Paton D. J., Lowings P. J. 1997. Detection and identification of ruminant and porcine pestiviruses by nested amplification of 5' untranslated cDNA regions. J Virol Methods 64: (1) 43–56.
12. Schneider, R., G. Unger, R. Stark, E. Schneider-Scherzer, and H.-J. Thiel. 1993. Identification of a structural glycoprotein of an RNA virus as a ribonuclease. Science 261: 1169–1171.
13. Thiel, H.-J., Plagemann, G. W., & Moennig, V. 1996. The pestiviruses. In Fields Virology, eds. Fields, B. N., Knipe, D. M., & Howley, P. M. (Lippincott-Raven, Philadelphia), pp.1059–1073.
14. Weiland, E., Thiel, H.-J., Hess, G., and Weiland, F. (1989). Development of monoclonal neutralizing antibodies against bovine viral diarrhea virus after pretreatment of mice with normal bovine cells and cyclophosphamide. J. Virol. Methods 24: 237–244.

EXAMPLES

Example 1

BVDV Fetal Challenge Study

Experimental Design

Six pregnant heifers were selected from a BVDV negative herd. Two groups of 3 heifers each were included in the trial. The animals in the groups were kept isolated, thereby insuring the absence of cross and outside infection.

TABLE 1

| Group No. | No. of animals | Virus | Application route | Dose per route $TCID_{50}$ |
|---|---|---|---|---|
| 1 | 3 | NCP7 | i.m.; i.n.; i.t.; s.c. | $1.2 \times 10^5$ |
| 2 | 3 | B-349-d | i.m.; i.n.; i.t.; s.c. | $1.2 \times 10^5$ |

Heifers from groups 1 to 2 were inoculated with at least $10^5$ $TCID_{50}$ BVDV in a volume of 3 ml per route. Application routes were intramuscular (i.m.), subcutaneous (s.c.), intranasal (i.n.) (1.5 ml per nostril) and intratracheal (i.t.).

Blood samples were collected from the animals for serology and virological examinations. Heifers were regularly monitored for the presence of clinical signs of BVDV infection during the observation period. The experiment was terminated after the birth of calves by examination for BVDV infection. Main evaluation parameters were the number of BVDV-related abortions and the number of calves born viraemic or comprising antibodies to BVDV.

Buffy Coat Preparations

Blood was collected in suitable sterile vessels pre-filled with heparin solution (Na-heparin for injection, 5000 IU/ml:Gedeon Richter RT, Budapest, Hungary) assuring at least 20 IU heparin per ml blood in the blood sample.

Blood was centrifuged for 10 min at 750 g at 4° C. Erythrocytes sedimented in the lower half of the tube while the plasma made up the supernatant in the upper half of the tube. On top of the erythrocyte phase, in the so called interface, the leukocytes were located. This thin layer of white blood cells was collected with a sterile pipette and then resuspended very carefully in a new tube filled up with Gey's buffer (140 mM $NH_4CL$, 2,7 mM KCl, 6,5 mM $Na_2HPO_4$, 1,5 mM $KH_2PO4$.). The suspension was kept on ice for 10 minutes. Cells were centrifuged again (10 min, 750 g, 4° C.) and the supernatant discarded. Gey's buffer treatment was repeated until no substantial amount of erythrocytes was observed in the suspension. Then the cells were washed twice in RPMI 1640 (Gibco BRL, Eggenstein, Germany) with 5% FCS (fetal calf serum, about 20 ml) and centrifuged thereafter. The obtained buffy coats were resuspended in a small volume (2 ml) of RPMI 1640 5% FCS and frozen at −70° C. in two aliquots of 1 ml. Buffy coats were used for the determination of blood cell associated BVDV.

BVDV Antibody ELISA-test

At least 10 ml fresh blood were collected at each sampling time point from each animal. Blood was allowed to clot at room temperature, and separated by centrifugation. Each serum sample was tested for the presence of BVDV-antibodies using a suitable and validated ELISA test (Svanovir™ BVDV antibody test Cat# 10 2200-10). The test was validated and performed according to the manufacturer's recommendations. Positive samples were diluted according to the $\log_2$ scale to determine BVDV antibody titers.

Fetal Infection Challenge Viruses

The strain B349-d was applied to group 2. It is almost identical to the NCP7 strain that was applied to group 1 except for one single deletion of the histidine in position 349 of its amino acid sequence. B349-d was prepared according to the procedure listed below.

Detection of BVDV From Buffy Coat or Tissue Samples by Virus Isolation Procedure Followed by an Indirect Immune Fluorescence Test (IFT)

For virus isolation a 20% suspension of tissues, serum, or buffy coat were used. 1 g organ material was homogenized using a mortar and pestle, diluted up to 5 ml phosphate buffered saline (PBS) and centrifuged at 1500*g for 10 minutes at 4° C. The supernatant was filtered sterilely using 0.45 μm filter holders, Schleicher and Schuell, Dassel, Germany, and used for virus isolation.

Virus propagation was performed on Marbin Darby Bovine Kidney cells (MDBK) as monolayer in 24 well plates with EMEM, containing 10% fetal calf serum, 1%, nonessential amino acids and 0,15% antibiotics. Before starting the cells were tested for contamination with BVDV by RT-nPCR as described below, and by immunofluorescence assay (IFA).

After splitting, the cells were each infected simultaneously with 100 μl suspension, serum or buffy coat in duplicates. 5 days later, one aliquot of the cell cultures was frozen and thawed.

100 μl of the cell lysate was passaged twice to MDBK cell suspensions. One aliquot was fixed with ethanol and stored at −20° C. for virus detection by immune fluorescence assay(IFA).

Infected cell cultures were tested by IFA. Cells were fixed by incubation with cold ethanol at −20° C. Fixed 24 well plates were washed with PBS twice. Afterwards the wells were incubated for two hours at room temperature with αBVDV-mAb-mix (Weiland et al. 1989). The αBVD-mAb-mix was diluted 1:10 in PBS. After washing three times with PBS rab.α-mouse FITC- conjugated antiserum (Jackson ImmunoResearch Laboratories Inc., West Grove, Pa. 19390, USA) was added in a solution of 1:150 in PBS (phosphate buffered saline) and incubated for 1 h at room temperature. After additional washing, glycerol-PBS (1:1) was added and stained cell cultures were investigated by immunofluorescence microscopy.

Detection of BVDV From Serum, Buffy Coat and Tissue Samples by Polymerase Chain Reaction (PCR)

RNA was extracted by column chromatography using QIAamp Viral Mini Kit for serum samples and RNeasy Mini Kit for organ material and buffy coat, according to the manufacturers recommendations. Both kits are available from Qiagen LTD, Hilden, Germany.

RT-nPCR:

Primer pairs for the detection of pestiviruses by RT-nPCR were used as previously described by Sandvik et al. (1997). The sequences of the external primers are:

(P103F) '5-TAG CCA TGC CCT TAG TAG GAC T-3' (SEQ ID NO: 1)

(P365R) '5-TGT GCC ATG TAC AGC AGA GAT T-3' (SEQ ID NO: 2)

The external primers generated a DNA- fragment of 280–284 bp length.

The sequences of the internal primers were as follows:

(B145F) '5-AAC AGT GGT GAG TTC GTT GGA T-3' (SEQ ID NO: 3)

(B314R) '5-CAC CCT ATC AGG CTG TAT TCG T-3' (SEQ ID NO: 4)

The internal primers generated a DNA- fragment of 191 bp length.

A volume of 5 μl total RNA (1 μg–1 pg) was used for RT-PCR amplification, using the Titan One Tube Kit, Boehringer Mannheim, Mannheim, Germany. RT-PCR was carried out in a total volume of 25 μl , containing 1*RT-PCR, 0,1 mM dNTPs, 20 pmol of sense and antisense primer, 5 mM dithiothreitol, 1 mM magnesium chloride, 2,5–5 U RNasin, Promega Ltd, 1–2,5 U enzyme mixture, AMV-RT and Taq Polymerase, ad 25 μl Aqua dest. including 0,1% diethylpyrocarbonat.

RT-PCR-cycle conditions were as follows:

42° C. for 1 hour, 95° C. for 5 min and 35 cycles of 94° C. for 1 min, 60° C. for 1 min and 72° C. for 1 min, finally prolongation for 10 min.

1 μl PCR product was used as template for the nested PCR, using Qiagen Taq (Qiagen LTD, Hilden, Germany).

nPCR was carried out in a total volume of 50 μl, containing 1*PCR buffer, 3,5 mM magnesium chloride, 0,1 mM dNTPs, 20 pmol of each primers and 2,5 U Taq.

The temperature profile of the nested PCR for 30 cycles was 94° C. for 1 min, 55° C. for 1 min and 72° C. for 1 min, followed by a prolonged last amplification.

A volume of 5 μl nPCR product was analysed by horizontal agarose gel electrophoresis in tris-acetate EDTA buffer, using 1% agarose and a 1 μg/ml ethidium bromid staining. The amplificate was identified by size comparison with a standard molecular weight 100 bp ladder (Gibco BRL, Eggenstein, Germany), the specificity of the PCR products was checked by sequence analysis.

To run non-crosscontaminating PCRs the RoboAmp 4200 (MWG Biotech, Ebersberg, Germany) was used for automated pipetting. Thermocycling was performed in a DNA Thermal Cycler Primus 96 (MWG Biotech, Ebersberg, Germany) or T3 (Biometra, Göttingen, Germany).

Results

Clinical Observation

No BVD related clinical signs were observed in Group 2 heifers during the observation period.

In Group 1, mostly increased salivation and nasal discharge were noticed for about a period of 6 days (between PI days 7–12). Two animals had diarrhea on day 14 PI. Results are summarized in table 2.

TABLE 2

| | Ranking of heifer No. in | | | | | |
|---|---|---|---|---|---|---|
| | Group 1 | | | Group 2 | | |
| Days PI | 11093 | 13178 | 11736 | 12031 | 10565 | 11060 |
| 1 | — | — | — | — | — | — |
| 2 | — | — | — | — | — | — |
| 3 | — | — | — | — | — | — |

TABLE 2-continued

Ranking of heifer No. in

| | Group 1 | | | Group 2 | | |
|---|---|---|---|---|---|---|
| Days PI | 11093 | 13178 | 11736 | 12031 | 10565 | 11060 |
| 4 | — | — | — | — | — | — |
| 5 | — | — | — | — | — | — |
| 6 | — | — | — | — | — | — |
| 7 | 3 | 2 | 2 | — | — | — |
| 8 | 3 | 2 | 2 | — | — | — |
| 9 | 3 | 2 | 2 | — | — | — |
| 10 | 2 | 2 | 2 | — | — | — |
| 11 | 1 | 1 | 1 | — | — | — |
| 12 | 1 | 1 | 1 | — | — | — |
| 13 | — | — | — | — | — | — |
| 14 | 2 | — | 1 | — | — | — |
| 15 | — | — | — | — | — | — |
| 16 | — | — | — | — | — | — |
| 17 | — | — | — | — | — | — |
| 18 | — | — | — | — | — | — |
| 19 | — | — | — | — | — | — |
| 20 | — | — | — | — | — | — |
| 21 | — | — | — | — | — | — |

Ranking: 1 = mild, 2 = moderate, 3 = severe

Pregnancy History

In Group 2, all heifers had a normal length of pregnancy (in a range of 270–277 days) and a pregnancy and parturition with no complication.

In Group 1, one animal (#11736) had abortion in the 8$^{th}$ month of pregnancy. Necropsy of the fetus revealed an acute sero-fibrinous inflammation of the chorion that led to an insufficient oxygen supply of the fetus and then to its suffocation. The remaining two animals gave birth to a calf after 278 (#13178) and 296 (#11093) days of pregnancy, respectively.

Virus Detection From Clinical Samples Obtained From Aborted Material or New Born Calves In case of an abortion, samples from different organs such as brain, spleen, or kidney were investigated by PCR and/or IFT for BVDV. All clinical samples obtained from the aborted fetus of cow 11736 in Group 1 were BVDV negative. Buffy coat samples from calves born from cows 11093 and 13178 were BVDV positive as confirmed by IFT and PCR. In contrast, buffy coats and serum samples from calves born from cows 10565, 110606, and 12031 of Group 2 were all negative for BVDV as confirmed by the above-mentioned methods. The data is summarized in Table 3.

TABLE 3

Fetal Transmission Evaluation

| group | Animal No. | chall. Virus | calf No. | abort/ life | conclusion from virus detection data | percentage placental transmission of group |
|---|---|---|---|---|---|---|
| 1 | 11093 | NCP7 | 11093 c | live | pos | 66% |
| | 11736 | | 11736 c | aborted | neg | |
| | 13178 | | 13178 c | live | pos | |
| 2 | 10565 | B349-d | 10565 c | live | neg | 0% |
| | 11060 | | 11060 c | live | neg | |
| | 12031 | | 12031 c | live | neg | |

Serological Data From Pregnant Cattle

At selection and day of infection the pregnant cows were BVDV negative. Serum samples from all animals in the trial collected 1 month after infection were BVDV seropositive. Serum positivity was confirmed for BVDV throughout the trial by reinvestigating serum samples obtained on a monthly basis from all animals. The data is summarized in table 4.

TABLE 4

ANTIBODY ELISA DATA

BVDV specific antibodies in sera taken at

| | | | | PI month | | | | | | At termination | |
|---|---|---|---|---|---|---|---|---|---|---|---|
| Cow No. | Group | Selection | Infection | 1 | 2 | 3 | 4 | 5 | 6 | cow | calf* |
| 11093 | 1 | − | − | + | + | + | + | + | + | + | − |
| 13178 | 1 | − | − | + | + | + | + | + | + | + | − |
| 11736 | 1 | − | − | + | + | + | + | Ab.° | NA | NA | NA |
| 11060 | 2 | − | − | + | + | + | + | + | + | + | − |
| 10565 | 2 | − | − | + | + | + | + | + | + | + | − |
| 12031 | 2 | − | − | + | + | + | + | + | − | − | − |

PI = Post infection; *before the first ingestion of colostrum;
NA = Not applicable;
° after abortion, cows were removed from the study, Ab. = abortion Discussion and Conclusion As 2 of 3 calves born in group 1 which were infected with NCP7 were viraemic for BVDV at birth whereas no calf born from group 2 which had been infected with B-349-d this data provides clear evidence that the genomic modification introduced in 349-d abrogates the ability of the parent virus NCP7 to induce fetal infection.

Example 2

Generation of RNase-negative BVDV Mutants

Starting with the full length cDNA clones pA/BVDV (Meyers et al., 1996b), from which infectious cRNA can be obtained by in vitro transcription, subclones were generated. A XhoI/BglII fragment from pA/BVDV was cloned into plasmid pCITE-2C, cut with the same enzymes. Single stranded plasmid DNA was produced from these constructs according to the method of Kunkel (Kunkel et al., 1987) using *E. coli* CJ 236 cells (BioRad) and the VCMS single strand phage (Stratagene). The single stranded DNA was converted to double strands using the 'Phagemid in vitro Mutagenesis Kit' (BioRad). A synthetic oligonucleotide which was used as a primer for generating the desired BVDV mutant is listed below in an exemplary fashion:

B-349-d: CATGAATGGAACAAAGGTTGGTG-CAACTGG (SEQ ID NO: 5)

The double stranded plasmid DNA was used for transformation of E.coli XL1-Blue cells (Stratagene). Bacterial colonies harboring plasmids were isolated via ampicillin selection. Plasmid DNA was prepared and further analyzed by nucleotide sequencing using the T7 polymerase sequencing kit (Pharmacia). Plasmids containing the desired mutations and no second site changes were used for the construction of full length cDNA clones. To obtain the BVDV CP7 mutant, a XhoI/BglII fragment containing the deletion was inserted into pA/BVDV cut with XhoI and NcoI together with a BglII/NcoI fragment isolated from pA/BVDV/Ins-. From construct pA/BVDV/Ins- a⁻cRNA was transcribed that gives rise to a noncytopathogenic BVDV upon transfection in suitable cells (Meyers et al., 1996b).

The different full length clones were amplified, and the plasmids isolated. The presence of the desired mutations was proven by DNA sequencing. After linearization with SmaI cRNA was transcribed as described previously (Meyers et al., 1996ab). RNA was purified by gel filtration and phenol/chloroform extraction and used for transfection of bovine kidney (MDBK clone B2) cells. The transfections were analyzed by immunofluorescence with virus specific antisera. The desired mutant could be recovered (as confirmed by immunofluorescence). The virus was amplified by passage on the same cell line used for the transfection experiments.

Further analysis of the mutant included determination of one step growth curves and characterization of viral RNA by Northern blot with virus specific cDNA probes as well as reverse transcription polymerase chain readtion (RT-PCR) and subsequent sequencing of the PCR fragments to verify the presence of the desired mutations in the viral genome. The recovered viruses grew equally well and produced similar amounts of RNA just as the virus resulting from the plasmid displaying the wild type sequence.

The viability of the BVDV mutant was shown by transfection of the respective cRNA and splitting of the cells 3 days thereafter. Part of the cells was seeded into a 3.5 cm diameter dish, fixed with acetone/methanol at the day thereafter and analyzed by immunofluorescence with a mixture of BVDV-specific monoclonal antibodies (Weiland et al., 1989). All cells were found positive whereas a control of cells transfected with noninfectious RNA showed no signal. From a part of the cells transfected with the respective cRNA, an extract was produced by one cycle of freezing and thawing. Fresh cells were infected with this cell extract and proved to be BVDV positive by BVDV specific immunofluorescence 3 days post infection.

Table 5 presents the changes introduced into the conserved sequences of $E^{RNS}$ representing the putative active site of the RNase which are encoded by the virus mutant.

TABLE 5

| Name | Sequence in RNase motif | RNase activity | Viability of mutant |
|---|---|---|---|
| pA/BVDV | ... SLHGIWPEKIC ... (SEQ ID NO: 6) | + | + |
| B-349-d | ... RHEWNKHGWCNW ... (SEQ ID NO: 7) ... SLHGIWPEKIC ... (SEQ ID NO: 6) ... RHEWNK_GWCNW ... (SEQ ID NO: 8) | − | + |

Legend to Table 5: Test for RNase activity was done in a transient assay. BHK21 cells were infected with Vaccina virus vTF7-3 (Fuerst et al, 1986) and then transfected with the respective cDNA construct (5 μg of plasmid DNA, transfection using Superfect as recommended by the supplier (Qiagen)). After 10 hours incubation at 37° C. in a $CO_2$ incubator, the transfected cells were lysed and processed for determination of RNase activity as described below). Viability was determined as described below.

Example 2

Effect of the Mutation in Position 349 of the BVDV Strain CP7 on the RNase Activity of $E^{RNS}$ For the BVDV mutant RNase activity was tested with material obtained after RNA transfection without passage of the recovered viruses. Cells transfected with the appropriate RNA were split 72 hours post transfection and seeded in two dishes. 24 hours later, from one dish, cell extracts were prepared and analyzed for RNase activity. Infection with wild type virus served as a positive control whereas noninfected cells were used as a negative control. Cells were washed twice with phosphate buffered saline and lysed in 0.4 ml of lysis buffer (20 mM Tris/HCl; 100 mM NaCl, 1 mM EDTA, 2 mg/ml bovine serum albumin; 1% Triton X100; 0.1% deoxycholic acid; 0.1% sodium dodecyl sulfate). The lysate was given into 1.5 ml reaction tubes, sonified (Branson sonifier B12, 120 Watt, 20 s in a cup horn water bath), cleared by centrifugation (5 minutes, 14,000 rpm, Eppendorf Centrifuge, 4° C.) and the supernatant subjected to ultracentrifugation (Beckmann table top ultracentifuge, 60 minutes at 4° C. and 45,000 rpm in a TLA 45 rotor). Determination of RNase activity was done in a total volume of 200 μl containing 5 or 50 μl of supernatant of the second centrifugation step and 80 μg of Poly(rU) (Pharmacia) in RNase-assay buffer (40 mM Tris-acetate (pH 6.5), 0.5 mM EDTA, 5 mM dithiothreitol (DTT)). After incubation of the reaction mixture at 37° C. for 1 hour 200 μl of 1.2 M perchloric acid, 20 mM $LaSO_4$ was added. After 15 minutes incubation on ice, the mixture was centrifugated for 15 minutes at 4° C. and 14,000 rpm in an Eppendorf centrifuge. To the supernatant, 3 volumes of water were added and an aliquot of the mixture was analyzed by measuring the optical density at 260 nm using an Ultrospec 3000 spectrophotometer (Pharmacia). The mutation introduced into the $E^{RNS}$ gene completely abrogated RNase activity (Table 6).

To prove infection, the cells of the second dish were analyzed by immunofluorescence with BVDV specific monoclonal antibodies (Weiland et al., 1989) and found 100% positive.

TABLE 6

|  | CP7 | B-349-d | control |
|---|---|---|---|
| OD$_{260}$ | 2.5 | 1.1 | 1.1 |

Description of table 6

CP7: virus recovered from pA/BVDV/Ins-; B-349-d: virus recovered from pA/B-349-d; control; extract from noninfected MDBK cells.

FIG. 1 Amino Acid Sequence of the Glycoprotein E$^{RNS}$ of BVDV CP VII (CP7) (SEQ D NO: 9)

1 ENITQWNLQDNGTEGIQRAMFQRGVNRSLHGIWPEKICTGVPSHLATDTE

51 LKAIHGMMDASEKTNYTCCRLQRHEWNKHGWCNWYNIEPWILLMNKTQAN

101 LTEGQPLRECAVTCRYDRDSDLNV-VTQARDSPTPLTGCKKGKNFSFAGIL

151 VQGPCNFEIAVSDVLFKEHDCTSVIQD-TAHYLVDGMTNSLESARQGTAKL

201 TTWLGRQLGILGKKLENKSKTWFGAYA

Sequences containing the residues conserved with regard to known RNases are underlined. The two histidine residues supposed to be in the catalytic centre of the enzyme are shown in bold characters. The shown sequence (SEQ ID NO: 9) corresponds to residues 271 to 497 of the CP$_7$ polyprotein.

What is claimed is:

1. A method of preventing fetal infection with bovine viral diarrhea virus (BVDV), pregnant cow infection with BVDV, or cow-to-calf transmission of BVDV, the method comprising administering to a pregnant cow a vaccine comprising a live attenuated BVDV, wherein the RNase activity residing in the glycoprotein $E^{RNS}$ of the live attenuated BVDV is inactivated.

2. The method according to claim 1, wherein the method prevents pregnant cow infection with BVDV.

3. The method according to claim 1, wherein the method induces fetal protection against BVDV infections in pregnant cows.

4. The method according to one of claims 1 to 3, wherein the BVDV infection is a BVDV type I infection.

5. The method according to one of claims 1 to 3, wherein the BVDV infection is a BVDV type II infection.

6. The method according to one of claims 1 to 3, wherein the RNase activity is inactivated by deletions and/or mutations of at least one amino acid of the glycoprotein $E^{RNS}$.

7. The method according to one of claims 1 to 3, wherein the live attenuated BVDV comprises a BVDV pestivirus, wherein the RNase activity is inactivated by the deletion of the histidine residue at position 349 of the glycoprotein $E^{RNS}$.

8. The method according to claim 4, wherein the RNase activity is inactivated by deletions and/or mutations of at least one amino acid of the glycoprotein $E^{RNS}$.

9. The method according to claim 5, wherein the RNase activity is inactivated by deletions and/or mutations of at least one amino acid of the glycoprotein $E^{RNS}$.

10. The method according to claim 4, wherein the live attenuated BVDV comprises a BVDV, wherein the RNase activity is inactivated by the deletion of the histidine residue at position 349 of the glycoprotein $E^{RNS.}$ 11. The method according to claim 5, wherein the live attenuated BVDV comprises a BVDV, wherein the RNase activity is inactivated by the deletion of the histidine residue at position 349 of the glycoprotein $E^{RNS.}$ 12. The method according to claim 6, wherein the live attenuated BVDV comprises a BVDV, wherein the RNase activity is inactivated by the deletion of the histidine residue at position 349 of the glycoprotein $E^{RNS}$.

13. The method according to claim 7, wherein the BVDV pestivirus is the CP7 strain.

14. The method according to claim 10, wherein the BVDV pestivirus is the CP7 strain.

15. The method according to claim 11, wherein the BVDV pestivirus is the CP7 strain.

16. The method according to claim 12, wherein the BVDV pestivirus is the CP7 strain.

* * * * *

SEQUENCE LISTING

```
<160> NUMBER OF SEQ ID NOS: 9

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 1
tagccatgcc cttagtagga ct                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 2
tgtgccatgt acagcagaga tt                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 3
aacagtggtg agttcgttgg at                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
caccctatca ggctgtattc gt                                              22

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer
```

<400> SEQUENCE: 5
catgaatgga acaaaggttg gtgcaactgg                                              30

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: RNase motif

<400> SEQUENCE: 6

Ser Leu His Gly Ile Trp Pro Glu Lys Ile Cys
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: RNase motif

<400> SEQUENCE: 7

Arg His Glu Trp Asn Lys His Gly Trp Cys Asn Trp
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: RNase motif

<400> SEQUENCE: 8

Arg His Glu Trp Asn Lys Gly Trp Cys Asn Trp
 1               5                  10

<210> SEQ ID NO 9
<211> LENGTH: 227
<212> TYPE: PRT
<213> ORGANISM: Artificial Sequence
<220> FEATURE:
<223> OTHER INFORMATION: Description of Artificial Sequence: BVDV
      glycoprotein E-rns

<400> SEQUENCE: 9

Glu Asn Ile Thr Gln Trp Asn Leu Gln Asp Asn Gly Thr Glu Gly Ile
 1               5                  10                  15

Gln Arg Ala Met Phe Gln Arg Gly Val Asn Arg Ser Leu His Gly Ile
                20                  25                  30

Trp Pro Glu Lys Ile Cys Thr Gly Val Pro Ser His Leu Ala Thr Asp
            35                  40                  45

Thr Glu Leu Lys Ala Ile His Gly Met Met Asp Ala Ser Glu Lys Thr
        50                  55                  60

Asn Tyr Thr Cys Cys Arg Leu Gln Arg His Glu Trp Asn Lys His Gly
    65                  70                  75                  80

Trp Cys Asn Trp Tyr Asn Ile Glu Pro Trp Ile Leu Leu Met Asn Lys
                85                  90                  95

Thr Gln Ala Asn Leu Thr Glu Gly Gln Pro Leu Arg Glu Cys Ala Val
                100                 105                 110

Thr Cys Arg Tyr Asp Arg Asp Ser Asp Leu Asn Val Val Thr Gln Ala
            115                 120                 125

-continued

```
Arg Asp Ser Pro Thr Pro Leu Thr Gly Cys Lys Lys Gly Lys Asn Phe
    130                 135                 140

Ser Phe Ala Gly Ile Leu Val Gln Gly Pro Cys Asn Phe Glu Ile Ala
145             150                 155                     160

Val Ser Asp Val Leu Phe Lys Glu His Asp Cys Thr Ser Val Ile Gln
                165                 170                 175

Asp Thr Ala His Tyr Leu Val Asp Gly Met Thr Asn Ser Leu Glu Ser
            180                 185                 190

Ala Arg Gln Gly Thr Ala Lys Leu Thr Thr Trp Leu Gly Arg Gln Leu
        195                 200                 205

Gly Ile Leu Gly Lys Lys Leu Glu Asn Lys Ser Lys Thr Trp Phe Gly
    210                 215                 220

Ala Tyr Ala
225
```